(12) United States Patent
Cavazza

(10) Patent No.: US 6,335,021 B1
(45) Date of Patent: *Jan. 1, 2002

(54) COMPOSITION FOR CONTROLLING MOOD DISORDERS IN HEALTHY INDIVIDUALS

(75) Inventor: Claudio Cavazza, Rome (IT)

(73) Assignee: Sigma-Tau HealthScience S.p.A., Pomezia (IT)

( * ) Notice: Subject to any disclaimer, the term of this patent is extended or adjusted under 35 U.S.C. 154(b) by 0 days.

This patent is subject to a terminal disclaimer.

(21) Appl. No.: 09/446,358

(22) PCT Filed: Jun. 12, 1998

(86) PCT No.: PCT/IT98/00157

§ 371 Date: Dec. 20, 1999

§ 102(e) Date: Dec. 20, 1999

(87) PCT Pub. No.: WO98/57629

PCT Pub. Date: Dec. 23, 1998

(30) Foreign Application Priority Data

Jun. 18, 1997 (IT) ........................................ RM97A0365

(51) Int. Cl.⁷ ................................................ A61K 7/00
(52) U.S. Cl. ........................ 424/401; 514/546; 514/547; 514/552; 514/419
(58) Field of Search .............................. 514/546, 547, 514/552, 419; 424/401

(56) References Cited

U.S. PATENT DOCUMENTS 5,977,162 A * 11/1999 Seidman ..................... 514/440
6,066,664 A * 5/2000 Cavazza ..................... 514/419

FOREIGN PATENT DOCUMENTS

| EP | 0 340 759 | 11/1989 |
| EP | 0340759 | * 11/1989 |
| JP | 08 283148 | 10/1996 |
| WO | 9855117 | * 12/1998 |

OTHER PUBLICATIONS

R. Bella, et al., "Effect of Acetyl-l-Carnitine on Geriatric Patients Suffering From Dysthymic Disorders", Int. J. Clin. Pharm. Res., vol. 10, No. 6, pp. 355–360, 1990. XP–002078732.

M. Durrmeyer, et al., "The Value of 5–HTP in the Treatment of Depression and Epilepsy. Clinical Study in the Adult", Psychologie Medicale, vol. 19, No. 2, pp. 381–393, 1978, Paris. XP–002078733 (English Abstract).

* cited by examiner

Primary Examiner—S. Mark Clardy
Assistant Examiner—Michael A. Williamson
(74) Attorney, Agent, or Firm—Oblon, Spivak, McClelland, Maier & Neustadt, P.C.

(57) ABSTRACT

The use of acetyl L-carnitine and its pharmacologically acceptable salts is disclosed for producing a composition suitable for controlling mood disorders mainly in young individuals who are not affected by permanent pathological CNS disturbances.

27 Claims, No Drawings

COMPOSITION FOR CONTROLLING MOOD DISORDERS IN HEALTHY INDIVIDUALS

The present invention relates to the use of acetyl L-carnitine and its pharmacologically accetable salts for producing a composition suitable for controlling mood disorders in individuals not presenting permanent pathological alterations of the central nervous system (CNS) by restoring the normal balance of neurotransmitter levels.

For the purposes of the present invention what is meant by "mood disorders" are those disorders which present as behavioural alterations of a depressive or manic type and, in particular, those disorders that present as oscillations between depressive and manic states alternating in the same individual. According to the present invention, these disorders also include the so-called premenstrual syndrome and states of bulimia.

Normal variations in mood (melancholy, mildly depressed states, anguish or joy and moderate excitement) constitute habitual aspects of daily life and must be distinguished from the pathological fluctuations of affective disorders.

Nevertheless, increasingly wide oscillations in affective attitudes and in that complex series of behavioural reactions and expressions, whether towards the self or towards external reality, which we define synthetically as "mood", would appear to affect an increasingly large population, consisting mainly of young individuals. Though the extent of such oscillations fails to reach the threshold of pathological relevance, this phenomenon is beginning to have substantial repercussions on important aspects of family life and on social and personal relations with profound consequences even of a socio-economic nature.

The main cause of this phenomenon probably has to do with the profound changes in lifestyle which have occurred, particularly with regard to young individuals, over a relatively short space of time.

Whereas, on the one hand, the opportunities for socialising (from travel and holidays even in far-off locations to attending public events and frequenting public meeting places, such as discotheques, aimed mainly at attracting a youthful population) have increased enormously compared to the past, amongst other things as a by-product of the boom in affluence, this phenomenon also presents worrying negative aspects such as the increased use of beverages with a strong alcohol content and the ever wider diffusion of psycho-active substances and of soft and hard drugs.

Set against the liberalisation of sexual habits and the increasingly widespread use and greater safety of contraceptive methods is the fear of sexually transmitted diseases, the most notable, of course, being AIDS, with its deterrent burden of anxiety which can have adverse repercussions on the normal expression of libido in both male and female subjects.

It is therefore hardly surprising that increasingly large numbers of the younger population are suffering from mood disorders.

These disorders which have a tendency to become chronic, but which exclude the precipitation of major or decidedly bipolar, cyclothymic depression disorders, are currently classified as dysthymias (DSM IV, 300.40) according to the definition provided by the authoritative Diagnostic and Statistical Manual of Mental Disorders (DSM IV) published by the American Psychiatric Association.

In these dysthymic individuals, who present a reduced social functional capability due to the chronic nature of their disorders, and certainly not as a result of the severity of their depressive or manic disturbances, there are often associated disorders of eating habits, with lack of appetite or bulimia, insomnia or hypersomnia, asthenia and fatigue, and reduced self-esteem, concentration and decision-making ability.

The attempts made to date to treat the mood disorders described above with well-known tricyclic antidepressants such as imipramine, nortriptyline, desipramine, amitriptyline etc., have failed to yield satisfactory results, whereas, in younger subjects particularly, their troublesome side effects such as sedation, dry mouth, tremors, postural vertigo, blurred vision, sweating and constipation are poorly tolerated.

It has now been found that acetyl L-carnitine and its pharmacologically acceptable salts constitute an effective means of treating the above-described mood disorders essentially without presenting any of the side effects typical of tricyclic antidepressants.

The object of the present invention thus consists in the use of acetyl L-carnitine or of one of its pharmacologically acceptable salts to produce a composition suitable for controlling mood disorders in individuals not presenting permanent pathological alterations of the central nervous system (CNS) by restoring the normal balance of neurotransmitter levels.

It is important to note that, since the subjects who are to receive the compositions of the present invention are essentially healthy and do not present fluctuations of pathological significance in their affective or mood disorders, the compositions of the invention may present themselves not only as pharmaceutical compositions, but also as health foods, medical foods or nutraceuticals, or as components of such products, containing other active ingredients, dietary supplements, vitamins, co-enzymes, mineral substances and the like in combination with acetyl L-carnitine.

The compositions of the invention are formulated, as regards their presentation form, nature of the unit dose form, weight and so on, in such a way as to favour administration of 500–3000 mg/day of acetyl L-carnitine or a molar equivalent amount of one of its pharmacologically acceptable salts to subjects who need it, either in a single dose or according to a multidose administration regimen.

In cases in which the subject suffering from a mood disorder, as defined in the context of the invention described herein, is also a bulimic or overweight subject (bulimia and depression often being associated manifestations in the same subject), the compositions may also advantageously include an effective amount of 5-hydroxy-tryptophane (5-HTP) in addition to acetyl L-carnitine or one of its pharmacologically acceptable salts.

Compositions suitable for such subjects are those which, as a result of their presentation form, type of unit dose form, weight and so on, favour the administration to the subject of 500–1500 mg/day of acetyl L-carnitine or a molar equivalent amount of one of its pharmacologically acceptable salts and 300–700 mg/day of 5-hydroxy-tryptophane.

The efficacy of acetyl L-carnitine for the treatment of mood disorders according to the invention has been demonstrated, amongst other things, by a clinical trial which will be described here below.

Clinical Trial

The selection of the patients for this trial consisted in a selection by exclusion, in which the medical history criterion was of paramount importance, with exclusion of all patients presenting episodes of major depression and cyclothymic manifestations classifiable as such on the basis of the DMS criteria.

Subjects were therefore recruited whose mood disorders had been dominated by dysphoric manifestations for at least 4 years, classifiable as dysthymia (DMS IV) and a depressive, irritable, cyclothymic personality or temperament on the basis of DMS IV and AXIS II. A total of 20 patients were selected, 12 males and 8 females, matching up to the above-mentioned criteria, and with a mean age of 26±2 years. Six patients (males) also complained of diminished libido and episodes of impotence, while the 8 female patients complained of loss of libido and anorexia. Eight patients (4 males) reported an increased intake of alcoholic beverages, without clinical complications, in the previous 8 months (mean intake 142±15 g/day) and 6 patients (1 male) reported bulimic episodes resulting in a mean weight gain of 2.1±0.5 kg over the previous 6 months.

Each patient was recruited into the study after 3 repeated visits, at monthly intervals, for the purposes of ruling out other concomitant pathologies or disorders according to DMS IV and AXIS II involving definite abuse of psychotropic substances. The objective neurological examination, current laboratory tests (SMA plus), ECG. BP and chest X-rays were all within normal limits.

None of the patients had been treated with SSRI or tricyclic antidepressants during the previous year. In the course of the month preceding the treatment with acetyl L-carnitine all treatments consisting in administration of benzodiazepines during the daytime were discontinued and only the administration of Lorazepam (2.5 mg) at 9 p.m. was allowed for all patients.

Each patient was administered acetyl L-carnitine 1 g per os twice daily (at breakfast- and lunch-time) for two months.

During the clinical interviews, at entry into the study, on day 45 of administration of acetyl L-carnitine and on day 90 (one month after the end of the treatment), patients were administered the following standardized rating scales: Hamilton Depression Rating Scale (HDRS), Hamilton Anxiety Rating Scale (HARS), Global Functional (or Social Adaptation) Rating (GFR).

For the recording of alcohol intake, a self-administered scale was used to record the alcohol-free days as a percentage of the total and the number of daily alcohol intakes, considering the intake of 10 grams as a single intake, in the month preceding treatment, during the treatment months and in the month following acetyl L-carnitine treatment.

The alcohol-free days during the two months of acetyl L-carnitine treatment numbered 16±3 on average, whereas in the baseline condition and in the month after treatment they numbered 6±2 and 8±2, respectively ($F=13.13$, $p<0.05$). The mean number of alcohol intakes was 6.1±2.1 as against 7.8±1.2 ($F=5.27$, $p<0.05$). All male patients reported the disappearance of symptoms of impotence and diminished libido 15 days after the start of acetyl L-carnitine treatment.

The table shows the findings obtained with the rating scales administered. The laboratory tests performed at the end of treatment yielded normal values; no significant changes as compared to pre-treatment conditions were found in laboratory tests. BP and ECG.

The results of the clinical trial demonstrate that acetyl L-carnitine significantly reduces expression of the depressive behavioural component in subjects suffering from dysthymic disorders. Reduction of the depressive component is the basic aim of drug therapy in these patients, in that the various disorders of social adaptation, such as bulimia or intake of psychotropic substances, are largely subordinate components of the chronic character disturbance, which by definition is unresponsive to the therapies commonly aimed at resolving major depressive or cyclothymic episodes.

|      | Basal      | Day 45     | Day 90     | F    | P      |
|------|------------|------------|------------|------|--------|
| HDRS | 13.9 ± 5.3 | 9.1 ± 4.8  | 12.8 ± 5.4 | 25.2 | <0.01  |
| HARS | 18.6 ± 3.8 | 12.8 ± 4.4 | 16.9 ± 5.0 | 24.3 | <0.05  |
| GFR  | 63.4 ± 6.6 | 75.3 ± 7.9 | 67.7 ± 6.8 | 19.8 | <0.05  |

The compositions of the invention can be obtained by mixing the active ingredient (acetyl L-carnitine or one of its pharmacologically acceptable salts, and, possibly, 5-HTP) with suitable excipients for the formulation of compositions which lend themselves to enteral administration (particularly oral) or to parenteral administration (particularly by the intramuscular or intravenous routes). All such excipients are well known to pharmacy experts.

What is meant by pharmacologically acceptable salt of acetyl L-carnitine is any salt of acetyl L-carnitine with an acid that does not give rise to unwanted side effects. These acids are well known to pharmacy experts.

Non-exclusive examples of such salts are chloride bromide, iodide, acid aspartate, acid citrate, tartrate and acid tartrate, acid phosphate, fumarate and acid fumarate, glycerophosphate, glucose phosphate, lactate, maleate and acid maleate, orotate, acid oxalate, acid sulphate, trichloroacetate, trifluoroacetate and methanesulphonate.

Here below are some examples of formulations in unit dosage form.

(a) Formulation for Tablets
   One tablet contains:

| Active ingredient | |
|---|---|
| acetyl L-carnitine Hcl (equivalent to 500 mg of acetyl L-carnitine, internal salt) Excipients | 590 mg |
| Microcrystalline cellulose, polyvinylpyrrolidone, magnesium stearate, cellulose acetate phthalate, diethylphthalate, dimethicone. | |

(b) Formulation for Intravenous Injectable Ampoules
   One lyophilized ampoule contains:

| Active ingredient | |
|---|---|
| acetyl L-carnitine, internal salt Excipients | 500 mg |
| mannitol | |
| One solvent ampoule contains: | |
| water for injections q.s. to 5 ml. | |

(c) Formulation for Sachets
   One sachet contains:

| Active ingredient | |
|---|---|
| acetyl L-carninne Hcl (equivalent to 500 mg acetyl L-carnitine, internal salt) Excipients | 590 mg |
| precipitated silica, saccharin sodium, hydroxypropylcelluose, sodium bicarbonate, tonic water (1 × 1000), mannitol. | |

(d) Formulation for Extemporary Solution
   One 12.316 g vial contains:

| Active ingredient | |
|---|---|
| acetyl L-carnitine Hcl (equivalent to 10.17 g base) | 12.0 g |

-continued

| Excipients |
| --- |
| methyl p-hydroxybenzoate, propyl p-hydroxybenzoate, polyvinylpyrrolidone. |

(e) Formulation for Capsules (Acetyl L-carnitine +5-HTP)

| Active ingredients | |
| --- | --- |
| acetyl L-carnitine, internal salt | 250 mg |
| 5-HTP | 250 mg |
| Excipients | |
| starch | 20 mg |
| mannitol | 30 mg |
| magnesium stearate | 3 mg |

What is claimed is:

1. A composition, comprising:
   acetyl L-carnitine or its pharmacologically acceptable salt;
   an excipient; and 5hydroxy-tryptophane.

2. The composition of claim 1, wherein said pharmacologically acceptable salt of acetyl L-carnitine is at least one salt selected from the group consisting of acetyl L-carnitine chloride, bromide, iodide, acid aspartate, acid citrate, tartrate and acid tartrate, acid phosphate, fumarate, acid fumarate, glycerophosphate, glucose phosphate, lactate, maleate, acid maleate, orotate, acid oxalate, acid sulphate, trichloroacetate, trifluoroacetate and methanesulphonate.

3. The composition according to claim 1, wherein said excipient is selected from the group consisting of microcrystalline cellulose, polyvinylpyrrolidone, magnesium stearate, cellulose acetate phtalate, diethylphtalate and dimethicone.

4. The composition according to claim 1, wherein said excipient is mannitol.

5. The composition according to claim 1, wherein said excipient is selected from the group consisting of precipitated silica, saccharin sodium, hydroxypropyl cellulose, sodium bicarbonate, tonic water and mannitol.

6. The composition according to claim 1, wherein said excipient is selected from the group consisting of methyl p-hydroxybenzoate, propyl p-hydroxybenzoate and polyvinylpyrrolidone.

7. The composition according to claim 1, further comprising at least one component selected from the group consisting of a nutraceutical, a dietary supplement, a vitamin, a co-enzyme and a mineral substance.

8. The composition according to claim 1, wherein said excipient is selected from the group consisting of starch, mannitol and magnesium stearate and combinations thereof.

9. The composition according to claim 1, further comprising at least one component selected from the group consisting of a nutraceutical, a dietary supplement, a vitamin, a co-enzyme and a mineral substance.

10. A method for treating a mood disorder, comprising:
    administering the composition according to claim 2 to a subject in need thereof, thereby restoring a neurotransmitter level.

11. The method according to claim 10, wherein a dose is 500–1500 mg/day of acetyl L-carnitine or a molar equivalent of its pharmaceutically acceptable salt and 300–700 mg/day of 5-hydroxy-tryptophane.

12. The method according to claim 10, wherein the mood disorder is a depressive or manic behavioral alteration.

13. The method according to claim 10, wherein a depressive state and a manic state alternate in said subject.

14. The method according to claim 10, wherein said subject is bulimic, overweight or both.

15. A method for treating a mood disorder, comprising:
    administering the composition according to claim 1 to a subject in need thereof, thereby restoring a neurotransmitter level.

16. The method according to claim 15, wherein a dose is 500–3000 mg/day of acetyl L-carnitine or a molar equivalent of its pharmaceutically acceptable salt.

17. The method according to claim 15, wherein the mood disorder is a depressive or manic behavioral alteration.

18. The method according to claim 15, wherein a depressive state and a manic state alternate in said subject.

19. The method according to claim 15, wherein a Hamilton Depression Rating Scale of said subject is decreased from a value of 13.9±5.3 before said administering to a value of 9.1±4.8 after said administering.

20. The method according to claim 15, wherein a Hamilton Anxiety Rating Scale of said subject is decreased from a value of 18.6±3.8 before said administering to a value of 12.8±4.4 after said administering.

21. The method according to claim 15, wherein a Global Function Rating of said subject is increased from a value of 63.4±6.6 before said administering to a value of 75.3±7.9 after said administering.

22. The method according to claim 15, wherein a Hamilton Depression Rating Scale of said subject is decreased from a value of 13.9±5.3 before said administering to a value of 12.8±5.4 after said administering.

23. The method according to claim 15, wherein a Hamilton Anxiety Rating Scale of said subject is decreased from a value of 18.6±3.8 before said administering to a value of 16.9±5.0 after said administering.

24. The method according to claim 15, wherein a Global Function Rating of said subject is increased from a value of 63.4±6.6 before said administering to a value of 67.7±6.8 after said administering.

25. A method, comprising:
    admixing acetyl L-carnitine or its pharmacologically acceptable salt with an excipient and with 5-hydroxy-tryptophane, thereby obtaining a composition.

26. The method of claim 25, wherein said pharmacologically acceptable salt of acetyl L-carnitine is at least one salt selected from the group consisting of acetyl L-carnitine chloride, bromide, iodide, acid aspartate, acid citrate, tartrate and acid tartrate, acid phosphate, fumarate, acid fumarate, glycerophosphate, glucose phosphate, lactate, maleate, acid maleate, orotate, acid oxalate, acid sulphate, trichloroacetate, trifluoroacetate and methanesulphonate.

27. The method of claim 25, wherein said excipient is selected from the group consisting of microcrystalline cellulose, polyvinylpyrrolidone, magnesium stearate, cellulose acetate phtalate, diethylphtalate, dimethicone, precipitated silica, saccharin sodium, hydroxypropyl cellulose, sodium bicarbonate, tonic water, mannitol, methyl p-hydroxybenzoate and propyl p-hydroxybenzoate.

* * * * *